United States Patent [19]

Ueda et al.

[11] Patent Number: 5,077,416
[45] Date of Patent: Dec. 31, 1991

[54] BENZODIFURANONE COMPOUNDS USEFUL FOR DYEING OR PRINTING HYDROPHOBIC FIBER MATERIALS AND PROCESS FOR THEIR PRODUCTION

[75] Inventors: Yasuyoshi Ueda; Jun Yamamoto, both of Osaka; Takashi Omura, Hyogo; Hideo Hattori; Shinei Ikeou, both of Osaka; Yosuke Yamamoto, Hyogo, all of Japan

[73] Assignee: Sumitomo Chemical Co. Ltd., Osaka, Japan

[21] Appl. No.: 408,064

[22] Filed: Sep. 15, 1989

[30] Foreign Application Priority Data

Dec. 1, 1988 [JP] Japan .................................. 63-305625

[51] Int. Cl.⁵ ..................... C09B 57/00; C07D 493/04; D06P 1/16
[52] U.S. Cl. ..................................... 549/299; 549/310
[58] Field of Search ........................................... 549/299

[56] References Cited

U.S. PATENT DOCUMENTS

| 4,115,404 | 9/1978 | Greenhalgh et al. | 549/299 X |
| 4,122,087 | 10/1978 | Greenhalgh et al. | 549/299 X |
| 4,650,882 | 3/1987 | Kenyon et al. | 549/299 |
| 4,680,417 | 7/1987 | Kenyon et al. | 549/299 |

FOREIGN PATENT DOCUMENTS

| 182507 | 5/1986 | European Pat. Off. | 549/299 |
| 252406 | 1/1988 | European Pat. Off. | 549/299 |
| 363034 | 4/1990 | European Pat. Off. | 549/299 |
| 2068402 | 8/1981 | United Kingdom | 549/299 |
| 2103231 | 2/1983 | United Kingdom | 549/299 |

OTHER PUBLICATIONS

"The Synthesis of Quinodimethanes in the Benzodifuranone and Benzodipyrrolidone Series", pp. 103-120 (1980) (Greenhalgh et al. IV).

Primary Examiner—Mary C. Lee
Assistant Examiner—Fiona T. Powers
Attorney, Agent, or Firm—Cushman, Darby & Cushman

[57] ABSTRACT

A heterocyclic compound of the formula,

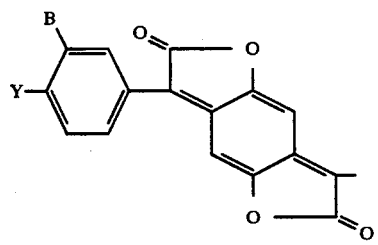

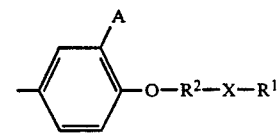

wherein A and B are each hydrogen, alkyl or alkoxy, Y is hydrogen, alkyl, alkoxy or $-O-R^2-X-R^1$, or Y and B are taken together with each other to form methylenedioxy, $R^1$ is alkyl, phenyl or alkenyl, $R^2$ is unsubstituted or substituted alkylene, and X is $-O-$, $-S-$, $-SO-$, $-SO_2-$ or

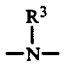

in which $R^3$ is hydrogen or alkyl, with the proviso that $R^1$ is $C_3$ or $C_4$ alkyl or alkenyl, or $C_1-C_4$ alkyl when $R^2$ is unsubstituted ethylene or propylene, respectively, X is $-O-$ or $-S-$, and Y and B don't form methylenedioxy, which is useful for dyeing or printing hydrophobic fiber materials with superior dyeability to give a dyed or printed product of a red color excellent in fastness properties, particularly those such as washing fastness.

9 Claims, No Drawings

BENZODIFURANONE COMPOUNDS USEFUL FOR DYEING OR PRINTING HYDROPHOBIC FIBER MATERIALS AND PROCESS FOR THEIR PRODUCTION

The present invention relates to heterocyclic compounds, their production and a process for dyeing or printing hydrophobic fiber materials therewith. More specifically, the present invention relates to benzodifuranone compounds useful for dyeing or printing hydrophobic fiber materials, for example, those such as polyester fibers and fiber materials containing the same, in a red color.

Disperse dyes useful for dyeing or printing the hydrophobic fiber materials have been increasingly desired to have much superior dyeability and capability of giving dyed or printed products excellent in various fastness properties with consumers' trend toward higher grade clothings. Answering such trend to increase the added value of dyed or printed products of hydrophobic fibers or hydrophobic fiber-containing fiber materials, they are often subjected to various after-finish treatments such as softening finish, antistatic finish, feel-improving finish and the like. However, these after-finish treatments usually carried out at relatively high temperatures encounter problems of dye bleed, so that the dyed or printed products deteriorate their wet fastness properties, particularly those such as washing fastness.

So far, many attempts to develop a red disperse dye capable of giving dyed or printed products excellent in washing fastness have been directed mainly toward azo compounds, so that many azo compounds have been proposed therefor. However, those known azo compounds are not yet sufficient to solve the problem such that the washing fastness of dyed or printed products becomes markedly poor after the finish treatments.

While, Published Unexamined Japanese Patent Applications No. 60-152567, No, 52-109526 and No. 56-122869 disclose various benzodifuranone compounds useful for dyeing or printing hydrophobic fiber materials. However, these benzodifuranone compounds expressly disclosed in such Patent Applications are also insufficient to satisfy both dyeability and the fastness properties at the same time, and still awaiting for improvements.

The present inventors have undertaken extensive studies to find a compound having excellent dye properties for dyeing or printing the hydrophobic fiber materials particularly those such as polyester fiber materials, and capable of giving dyed or printed products excellent in fastness properties such as light fastness, sublimation fastness and wet fastness, particularly those such as washing fastness, and as a result attained to the present invention.

The present invention provides a heterocyclic compound of the following formula (I),

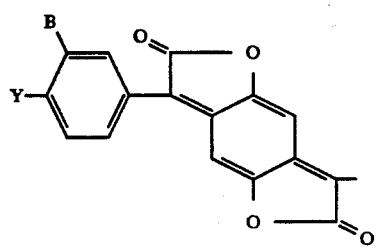

-continued

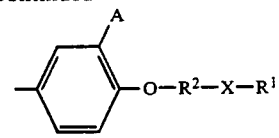

wherein A and B are each independently a hydrogen atom, a $C_1$-$C_4$ alkyl group or a $C_1$-$C_4$ alkoxy group; Y is a hydrogen atom, a $C_1$-$C_4$ alkyl group, a $C_1$-$C_4$ alkoxy group or a group of —O—$R^2$-X-$R^1$, or Y and B are taken together with each other to form a methylenedioxy group; $R^1$ is a $C_1$-$C_4$ alkyl group, a phenyl group or a $C_3$ or $C_4$ alkenyl group; $R^2$ is an ethylene group unsubstituted or substituted by a methyl, methoxyymethyl or ethoxymethyl group, a propylene group unsubstituted or substituted by a hydroxy, $C_1$-$C_4$ alkylcarbonyloxy or methyl group, or a $D_4$-$D_8$ alkylene group unsubstituted or substituted by a hydroxy, $C_1$-$C_4$ alkylcarbonyloxy or $C_1$-$C_4$ alkoxy group; and X is a divalent group of —O—, —S—, —SO—, —SO$_2$— or

in which $R^3$ is a hydrogen atom or a $C_1$-$C_4$ alkyl group; with the proviso that when X is a divalent group of —O— or —S— and Y and B are not taken together with each other to form a methylenedioxy group, and when $R^2$ is unsubstituted ethylene or unsubstituted propylene group, $R^1$ is a $C_3$ or $C_4$ alkyl or alkenyl group, or a $C_1$-$C_4$ alkyl group, respectively.

The present invention also provides a process for producing the heterocyclic compound of the formula (I), which comprises reaching a mandelic acid of the following formula (II),

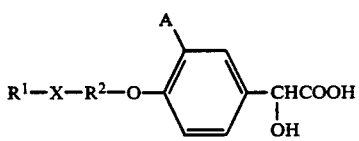

wherein A, X, $R^1$ and $R^2$ are as defined above, with a compound of the following formula (III),

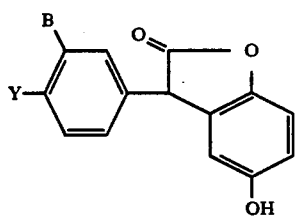

wherein B and Y are as defined above, followed by mild oxidation.

The present invention further provides a process for dyeing or printing hydrophobic fiber materials, which comprises contacting the fiber materials with the heterocyclic compound of the formula (I).

In the above formula (I), the alkyl group represented by A or B includes, for example, methyl, ethyl, n-propyl, i-propyl, n-butyl and the like, and the alkoxy group represented thereby includes, for example, methoxy, ethoxy, n-propoxy, n-butoxy, sec-butoxy and the like.

In the present invention, A is preferably hydrogen, methyl or methoxy, and more preferably hydrogen, and B is preferably hydrogen and the alkoxy such as methoxy and butoxy, more preferably hydrogen.

The alkyl and alkoxy groups represented by Y include those exemplified above for the symbols A and B. In the present invention, Y is preferably hydrogen, methyl, alkoxy such as methoxy and butoxy, $C_1$–$C_4$ alkoxy-$C_2$ or $C_3$ alkoxy which is represented by —O—$R^2$—X—$R^1$ and includes, for example, methoxypropoxy, and methylenedioxy formed together with B. Of these, particularly preferable Y is hydrogen.

With respect to the symbols $R^1$ and $R^2$, preferred embodiments are as follows;

a. $R^2$ is unsubstituted ethylene, and $R^1$ is straight or branched $C_3$ or $C_4$ alkyl such as n-propyl, iso-propyl, n-butyl and iso-butyl.

b. $R^2$ is ethylene substituted by methyl, methoxymethyl or ethoxymethyl, and $R^1$ is $C_1$–$C_4$ alkyl, particularly such as methyl and ethyl.

c. $R^2$ is unsubstituted propylene, and $R^1$ is $C_1$–$C_3$ alkyl such as methyl, ethyl and n-propyl, particularly preferably ethyl.

d. $R^2$ is propylene substituted by hydroxy or methyl, and $R^1$ is $C_1$–$C_3$ alkyl such as methyl, ethyl and n-propyl, or $C_3$ or $C_4$ alkenyl such as alkyl.

e. $R^2$ is straight $C_4$–$C_8$ alkylene unsubstituted or substituted by hydroxy, $C_1$–$C_4$ alkylcarbonyloxy or $C_1$–$C_4$ alkoxy, and $R^1$ is $C_1$–$C_3$ alkyl such as methyl, ethyl and n-propyl.

Of these, b and c are particularly preferred.

Among the divalent groups represented by X, particularly preferred is —O—.

The heterocyclic compound of the formula (I) can be produced in a manner known per se, for example, by reacting the mandelic acid of the formula (II) with the compound of the formula (III), followed by mild oxidation. The reaction can be readily effected in a solvent at a temperature of about 50° C. to about 150° C. Oxidants preferably usable for the oxidation includes chloranil, persulfates, hydrogen peroxide and the like.

The mandelic acid of the formula (II) can be produced in a manner described in, for example, System No. 1106/H410-411, Vol. 10 of Beilsteins Handbuch der Organischen Chemie and enlarged eddition thereof. According to the description, a 4-hydroxymandelic acid of the following formula (II)a,

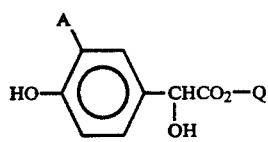
(II)a wherein A is as defined above, and Q is a hydrogen atom or a $C_1$–$C_4$ alkyl group, and an alkylating agent of the following formula (II)b,

(II)b wherein $R^1$, $R^2$ and X are as defined above, and L is a splittable group such as a halogen atom, an arylsulfonyloxy group and the like, can be allowed to react with each other in the presence of an acid binding agent, if necessary, followed by hydrolysis of the ester bonding.

Alternatively, the mandelic acid (II) can be also produced by reacting a benzaldehyde of the following formula (II)c,

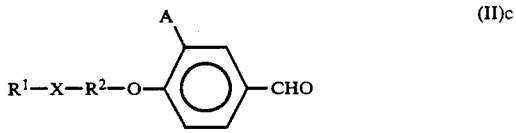
(II)c wherein $R^1$, $R^2$, X and A are as defined above, with sodium hydrogensulfite and sodium cyanide, and then hydrolyzing the resulting mandelonitrile, or by reducing a phenylglyoxylic acid of the following formula (II)d,

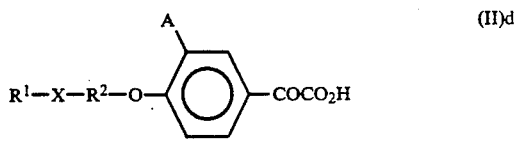
(II)d wherein $R^1$, $R^2$, X and A are as defined above.

The compound of the formula (III) can be produced in a manner described in, for example, Chemische Berichte, Vol. 30, 124(1897), such that a mandelic acid compound of the following formula (III)a,

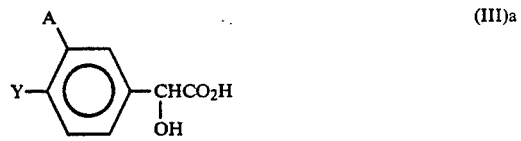
(III)a wherein A and Y are as defined above, and hydroquione are allowed to react with each other in an acid medium such as 73% sulfuric acid under heating. In this manner, the starting compound of the formula (III)a can be produced in a manner similar to that for the production of the compound (II).

The heterocyclic compound of the formula (I) in accordance with the present invention is useful for dyeing or printing hydrophobic fiber materials, particularly those such as polyester fiber materials. In utilizing the present heterocyclic compound in such field. The compound (I) can be finely pulverized in an aqueous medium with the aid of naphthalenesulfonic acid/formaldehyde condensate, lignin sulfonic acid or the like, thereby obtaining a liquid dye dispersion. The liquid dye dispersion can be used as it is for the dyeing or printing of fiber materials, or dried with, for example, a spray drier to be made in a powder form.

Dyeing can be carried out by a high temperature dyeing method wherein hydrophobic fiber materials are dipped in an aqueous dye bath and heated to a temperature of 105° C. or higher, preferably 110° C. to 140° C. under increased pressure, a carrier dyeing method wherein dyeing is carried out in the presence of a carrier such as o-phenylphenol, trichlorobenzene and the like at a relatively high temperature, for example, water-boiling temperature, or a thermosol method wherein the fiber materials are padded with an aqueous dye dispersion and dry-heated at a temperature of 150° to 230° C. for 30 to 60 seconds.

Printing can be carried out by mixing the aqueous dye dispersion with a suitable stock paste to obtain a color paste, printing fiber materials with the color paste and then steaming or thermosol-treating the printed fiber materials.

In addition, the fiber materials can also be dyed by a solvent dyeing method wherein an organic solvent such as trichloroethylene, perchloroethylene and the like is used as a dyeing medium.

The dyed or printed products thus obtained can be subjected, if desired, to after-finish treatments such as softening finish, water-repellenting finish, feel-improving finish, antistatic finish, sanitary finish and the like, in a conventional manner.

The present heterocyclic compound of the formula (I) can be characterized by the facts such that hydrophobic fiber materials, particularly those such as polyester fiber materials, can be dyed or printed in a usual manner using the present compound (I), thereby obtaining dyed or printed products of a brilliant red color excellent in various fastness properties such as light fastness, sublimation fastness, wet fastness and the like, and such fastness properties cannot be deteriorated even after heat-set treatment and after-finish treatments. For example, the fiber materials can be dyed using a high concentration of the dye to obtain dyed products of a deep color (e.g. JIS 2/1 depth), and the washing fastness property thereof is robust so that it can be kept at a higher degree even after the heat-set treatments of dyed products than that of those dyed with existing red disperse dyes. Considering the fact that a standard of the washing fastness has been made severer to meet the actual condition of consumers' high demand, the robustness is significant.

The present heterocyclic compound of the formula (I) can be characterized also by superior dyeability such as dyeing power and build-up property, so that dyed or printed products of a deep color can be readily obtained, particularly by the high temperature dyeing method. Moreover, the present compound can be used in combination with other dyes to improve the dye performance and to obtain a variety of color.

In consideration of the characteristic features described above, the heterocyclic compound of the present invention can be advantageously used particularly for the dyeing of apparels such as sportswear, which are required to be dyed usually in a deep color and have superior washing fastness because they are to be washed again and again.

The present invention is illustrated in more detail with reference to the following Examples, which are only illustrative but not limitative for the scope of the present invention. In Examples, parts are by weight.

EXAMPLE 1

A mixture of 4-(2-n-butoxyethoxy)mandelic acid (2.82 parts) and 5-hydroxy-2-oxo-3-phenyl-2,3-dihydrobenzofuran (2.26 parts) was kept at 110° C. for 9 hours in a mixed solvent of acetic acid (38 parts) and sulfuric acid (2 parts), and thereafter, ammonium persulfate (2.34 parts) was added to the reaction mixture. The resulting mixture was kept at 110° C. for additional 1 hour, thereafter cooled to ambient temperature, and then poured into ice water. The crystals produced were collected on a filter, washed and dried to obtain a compound of the following formula.

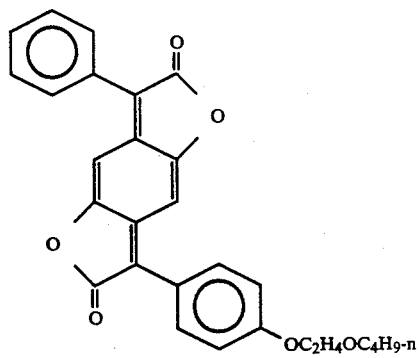

The maximum absorption wave length ($\lambda$max) of the compound in dimethylformamide was found to be 502 nm.

EXAMPLE 2

The compound obtained in Example 1 (0.1 part) was finely pulverized in an aqueous medium with the aid of naphthalenesulfonic acid-formaldehyde condensate (3.0 parts). The resulting dye dispersion was dried to form powder.

Polyester cloth (10 parts, Tetron jersey, a product of Teijin Limited, in Japan) was dipped in a dyebath containing the powder (0.6 part), and dyeing was continued for 60 minutes at 130° to 135° C. under increased pressures. The dyed cloth was subjected to reduction-rinsing treatment at 85° C. for 10 minutes in a solution of sodium hydroxide (3 parts), hydrosulfite (3 parts) and a betaine amphoteric surfactant (3 parts) in water (3000 parts), washed with water and then dried, thereby obtaining a dyed product of a brilliant red color superior in light fastness, sublimation fastness and wet fastness.

The dyed product was dipped in a padding liquor containing a soft-finishing agent (10 g/l Sumitex Softener LK-1, a product of Sumitomo Chemical Co., Ltd, in Japan) and an anti-static agent (5 g/l, Sumistat F-1, a product of Sumitomo Chemical Co., Ltd., in Japan), squeezed uniformly at a pick-up of 80%, again dipped into the same padding liquor as above, squeezed at the same level as above, pre-dried at 80° C. for 2 minutes and then subjected to heat set at 170° C. for 1 minute. The thus after-finished dyed product was found to have a superior washing fastness.

EXAMPLE 3

The compound obtained in Example 1 (1.3 parts) was finely pulverized with the aid of lignin sulfonic acid (3.7 parts). To the resulting dispersion were added hot water (35 parts) and a half emulsion paste (60 parts) having the following composition.
O/W Emulsion 300 parts
Stock paste (12% Maypro gum) 694 parts
Sodium Chlorate 4 parts
Tartaric acid 2 parts Polyester cloth (Tetron tropical, a product of Teijin Limited in Japan) was printed with the above obtained printing paste, pre-dried and steamed for 7 minutes at 170° C. under atmospheric pressure. The printed cloth was subjected to reduction rinsing treatment, washing with water and softening and anti-static finishings in this order in a manner similar to that of Example 2. The thus obtained printed product of a red color was found to have superior light, sublimation and wet fastness properties, particularly washing fastness.

EXAMPLE 4

Example 1 was repeated, provided that 4(3-ethoxypropoxy)mandelic acid (2.67 parts) was used in place of 4-(2-n-butoxyethoxy)mandelic acid (2.82 parts), thereby obtaining a compound of the following formula ($\lambda_{DMF}^{max}$ 503 nm).

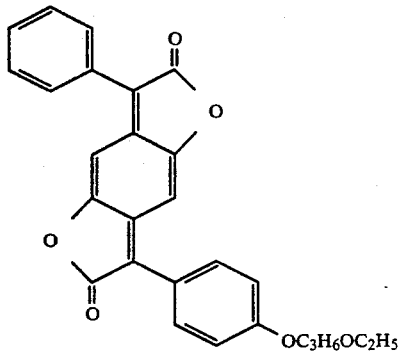

Using the compound, Example 2 was repeated to obtain a dyed product superior in light, sublimation and wet fastness properties, particularly superior in washing fastness.

EXAMPLES 5 TO 33

In a manner similar to that of Example 1, respective compounds as shown in the following table was obtained. These compounds can be used for dyeing polyester cloth to obtain dyed product having superior washing fastness.

TABLE

| Example No. | A | B | Y | $R^1$ | X | $R^2$ | DMF $\lambda_{max}$ (nm) |
|---|---|---|---|---|---|---|---|
| 5 | H | H | H | n-$C_3H_7$ | O | —$(CH_2)_3$— | 503 |
| 6 | H | H | H | $(CH_3)_2CHCH_2$ | O | —$C_2H_4$— | 502 |
| 7 | H | H | H | $CH_3$ | O | —$(CH_2)_4$— | 505 |
| 8 | H | H | $CH_3O$— | n-$C_3H_7$ | O | —$(CH_2)_3$— | 526 |
| 9 | H | H | $CH_3$ | n-$C_3H_7$ | O | —$C_2H_4$— | 510 |
| 10 | H | H | H | $CH_2$=$CHCH_2$— | O | —$CH_2CHCH_2$— <br> \|<br>OH | 503 |
| 11 | H | H | H | $CH_3$<br>\|<br>$CH_2$=$CHCH_2$— | O | —$C_2H_4$— | 501 |
| 12 | $CH_3O$— | H | H | $C_2H_5$ | O | —$(CH_2)_3$— | 516 |
| 13 | H | $CH_3$ | $CH_3$ | (phenyl) | O | —$CH_2CHCH_2$—<br>\|<br>$OCOC_2H_5$ - | 513 |
| 14 | H | H | H | n-$C_3H_7$ | S | —$(CH_2)_3$— | 504 |
| 15 | H | H | H | n-$C_3H_7$ | SO | —$(CH_2)_3$— | 502 |
| 16 | H | $CH_3O$ | $CH_3O$ | n-$C_3H_7$ | $SO_2$ | —$(CH_2)_3$— | 514 |
| 17 | $CH_3$ | H | H | n-$C_3H_7$ | NH | —$(CH_2)_3$— | 507 |
| 18 | H | H | H | $C_2H_5$ | N—$C_2H_5$ | —$(CH_2)_3$— | 502 |
| 19 | H | H | H | n-$C_4H_9$ | N—$C_4H_9$-n | —$C_2H_4$— | 503 |
| 20 | H | H | H | n-$C_3H_7$ | O | $CH_2OCH_3$<br>\|<br>—$CH_2CH$— | 503 |
| 21 | H | —$OCH_2O$— | | $C_2H_5$ | O | —$(CH_2)_3$— | 514 |

TABLE-continued

![structure]

| Example No. | A | B | Y | R¹ | X | R² | DMF $\lambda_{max}$ (nm) |
|---|---|---|---|---|---|---|---|
| 22 | H | H | n-$C_4H_9O$— | $C_2H_5$ | O | —$CH_2CH$— $\vert$ $CH_3$ | 528 |
| 23 | H | H | $CH_3OC_3H_6O$— | $CH_3$ | O | —$(CH_2)_3$— | 529 |
| 24 | H | H | $(CH_3)_2CH$— | $CH_3$ | O | —$(CH_2)_3$— | 510 |
| 25 | H | $C_2H_5CH$—O— $\vert$ $CH_3$ | H | $CH_3$ | O | —$CH_2CH$— $\vert$ $CH_2OCH_3$ | 505 |
| 26 | H | H | H | $CH_3$ | O | —$(CH_2)_5$— | 503 |
| 27 | H | H | H | $C_2H_5$ | O | —$(CH_2)_5$— | 503 |
| 28 | H | H | H | $CH_3$ | O | —$(CH_2)_6$— | 503 |
| 29 | H | H | H | $C_2H_5$ | O | —$(CH_2)_6$— | 503 |
| 30 | H | H | H | $CH_3$ | O | —$(CH_2)_4CHCH_2$— $\vert$ OH | 503 |
| 31 | H | H | H | n-$C_3H_7$ | O | —$CH_2CH_2CH$— $\vert$ $CH_3$ | 503 |
| 32 | H | H | H | $CH_3$ | O | —$CH_2CH$— $\vert$ $CH_2OCH_3$ | 503 |
| 33 | H | H | H | $CH_3$ | O | —$CH_2CH$— $\vert$ $CH_2OC_2H_5$ | 503 |

We claim:
1. A heterocyclic compound of formula (I):

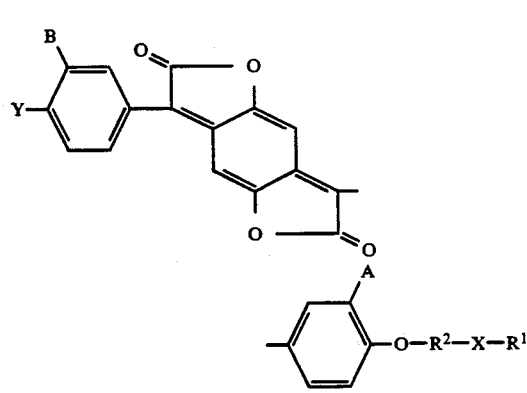

(I)

wherein A, B, and Y are each hydrogen; R¹ is $C_1$-$C_4$ alkyl, phenyl or $C_3$ or $C_4$ alkenyl; R² is ethylene substituted by methyl, methoxymethyl or ethoxymethyl, unsubstituted propylene, or $C_4$-$C_8$ alkylene unsubstituted or substituted by hydroxy, $C_1$-$C_4$ alkylcarbonyloxy or $C_1$-$C_4$ alkoxy; and X is —O—; with the proviso that R¹ is $C_1$-$C_4$ alkyl when R² is unsubstituted propylene.

2. The compound according to claim 1, wherein R¹ is methyl, ethyl or n-propyl and R² is unsubstituted propylene.

3. The compound according to claim 2, which is represented by the following formula,

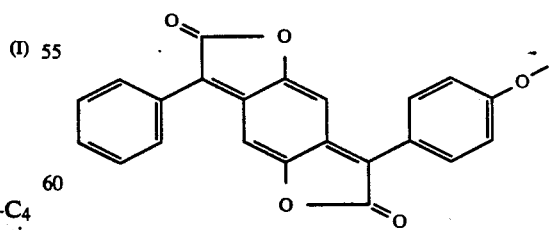

$CH_2CH_2CH_2OCH_2CH_2CH_3$.

4. The compound according to claim 2, which is represented by the following formula,

5. The compound according to claim 1, which is represented by the following formula,

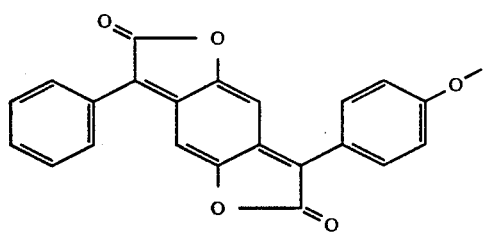
CH₂CH₂CH₂OCH₂CH₂CH₃.

6. The compound according to claim 1, which is represented by the following formula,

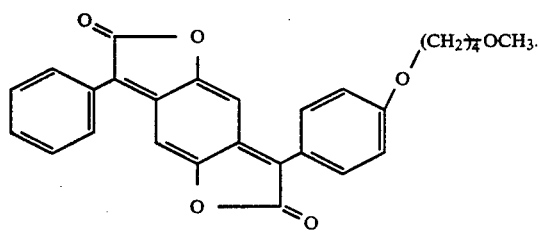
O—(CH₂)₄OCH₃.

7. The compound according to claim 1, which is represented by the following formula,

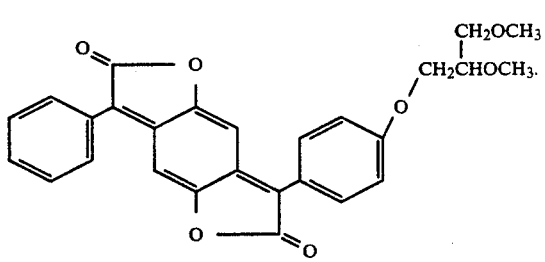
$$O-CH_2CHOCH_3 \atop |\phantom{xx} CH_2OCH_3$$

8. The compound according to claim 1, which is represented by the following formula,

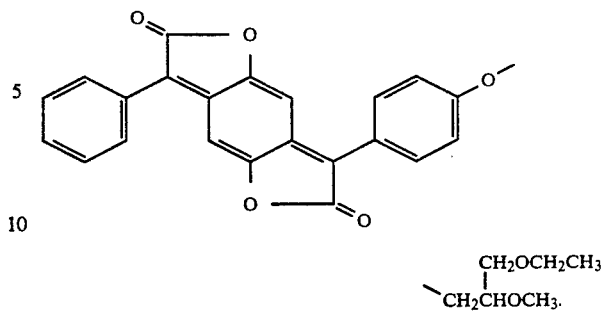
$$CH_2CHOCH_3 \atop |\phantom{xx} CH_2OCH_2CH_3$$

9. The compound according to claim 1, which is represented by the following formula,

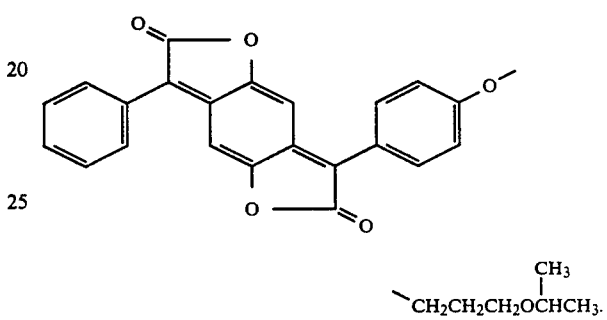
$$CH_2CH_2CH_2OCHCH_3 \atop \phantom{xxxxxxxxxxxx}|\phantom{x} CH_3$$

9. The compound according to claim 2, which is represented by the following formula,

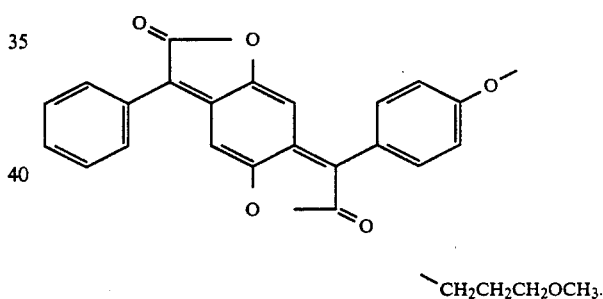
CH₂CH₂CH₂OCH₃.

* * * * *